(12) United States Patent
Ki et al.

(10) Patent No.: US 10,801,935 B2
(45) Date of Patent: Oct. 13, 2020

(54) SYSTEM AND METHOD FOR DETERMINING A CONE INDEX VALUE

(71) Applicant: DEERE & COMPANY, Moline, IL (US)

(72) Inventors: Nohoon Ki, Cedar Falls, IA (US); Andy B. Appleton, Cedar Falls, IA (US); Wissam H. El-Ratal, Cedar Falls, IA (US); Rui Zhang, Cedar Falls, IA (US); Justin T. Roth, Cedar Falls, IA (US)

(73) Assignee: DEERE & COMPANY, Moline, IL (US)

( * ) Notice: Subject to any disclaimer, the term of this patent is extended or adjusted under 35 U.S.C. 154(b) by 363 days.

(21) Appl. No.: 15/872,341

(22) Filed: Jan. 16, 2018

(65) Prior Publication Data

US 2019/0219489 A1    Jul. 18, 2019

(51) Int. Cl.
| | |
|---|---|
| *G06F 11/30* | (2006.01) |
| *G01N 3/42* | (2006.01) |
| *E02D 1/02* | (2006.01) |
| *G01N 33/24* | (2006.01) |

(52) U.S. Cl.
CPC .............. *G01N 3/42* (2013.01); *E02D 1/022* (2013.01); *G01N 33/24* (2013.01)

(58) Field of Classification Search
CPC ........................................................ G01N 3/42
See application file for complete search history.

(56) References Cited

U.S. PATENT DOCUMENTS

| | | | |
|---|---|---|---|
| 2016/0200154 A1* | 7/2016 | Steinmeyer | ........... B60C 23/061 702/50 |
| 2017/0227969 A1* | 8/2017 | Murray | .................. A01D 42/00 |

FOREIGN PATENT DOCUMENTS

DE      102010011124 A1    12/2011

OTHER PUBLICATIONS

Nam, Ju S.; Park, Young J.; Kim, Kyeong U,: "Determination of rating cone index using wheel sinkage and slip", in Journal of Teramechanics, vol. 47, 2010, No. S. 243-248-ISSN 0022-4898 (Year: 2010).*
German Search Report, German Patent and Trademark Office, dated Oct. 4, 2019, DE 102018218635.9, 12 pages.
Fan Yang, Guoyu Lin, Weigong Zhang: Terrain Classification for terrain parameter estimation based on a dynamic testing system; Sensor Review, 35, 2015, 4, 329-339; https://www.emerald.com/insight/content/doi/10.1108/SR-01-2015-003/full/pdf?title=terrain-classification-for-terrain-parameter-estimation-based-on-a-dynamic-testing-system.
Laughery, Sean; Gerhart, Grant; Goetz, Richard: Bekker's Terramechanics Model for Off-Road Vehicle Research. 1990, https://apps.dtic.mil/dtic/tr/fulltext/u2/a457955.pdf.
Nam, Ju S.; Park, Young J.; Kim, Kyeong U.: Determination of rating cone index using wheel sinkage and stip. In: Journal of Teramechanics, vol. 47, 2010, No. 4, S. 243-248.-ISSN 0022-4898.

* cited by examiner

*Primary Examiner* — Phuong Huynh
(74) *Attorney, Agent, or Firm* — Taft Stettinius & Hollister LLP; Stephen F. Rost

(57) ABSTRACT

A work machine with a chassis, a wheel hub rotationally coupled to the chassis, a tire coupled to the wheel hub and configured to engage an underlying surface, and a controller communicating with a plurality of sensors and having a memory unit. Wherein, the controller stores tire data for the tire in the memory unit and the controller determines a cone index of the underlying surface of the work machine based on the tire data and the plurality of sensors.

20 Claims, 6 Drawing Sheets

SYSTEM AND METHOD FOR DETERMINING A CONE INDEX VALUE

FIELD OF THE DISCLOSURE

The present disclosure relates to determining a cone index value of soil, and in particular, to actively determining the cone index value of soil with a work machine while traveling thereon.

BACKGROUND OF THE DISCLOSURE

Many work machines travel along an underlying surface or field as they perform a work function. Often, the work function includes pulling or pushing implements or the like coupled to the work machine. Alternatively, sometimes the work machine may have cargo stored thereon as it performs the work function. Regardless of the work function, it is advantageous to have the work machine performing at the highest possible efficiency during the work function to conserve energy and quickly complete the work function. One of the primary factors contributing to the efficiency of the work machine executing the work function is the traction of ground-engaging mechanisms of the work machine against the underlying surface.

The amount of traction between the work machine and the underlying surface is often modified by altering certain conditions of the work machine. For example, a tire pressure of any tires on the work machine may be altered in order to allow better traction between the work machine and the underlying surface. Further still, ballast weight and location is frequently modified to create ideal traction for the work machine in view of the particular work function being executed. In another example, an electric hybrid system may be used to power ground engaging mechanisms of the implement.

The ideal operating conditions for these systems depends on the consistency of the underlying surface. In one example, a soft and sandy underlying surface requires low tire pressures to ensure proper traction is achieved for the work function. Alternatively, on a hard underlying surface relatively high tire pressures are utilized to provide an optimal traction and efficient execution of the work function.

One method for determining the properties of the underlying surface is to determine the cone index prior to executing the work function. The cone index represents the mechanical properties of the underlying surface and is frequently determined by measuring the soil penetration resistance. Often, to determine the cone index of any particular area, a cone penetrometer or the like is used. The cone penetrometer is driven into the ground at locations throughout the field to identify the cone index variance throughout.

SUMMARY

One embodiment is a work machine having a chassis, a wheel hub rotationally coupled to the chassis, a tire coupled to the wheel hub and configured to engage an underlying surface, and a controller communicating with a plurality of sensors and having a memory unit. Wherein, the controller stores tire data for the tire in the memory unit. Further wherein, the controller determines a cone index of the underlying surface of the work machine based on the tire data and the plurality of sensors.

In one example of this embodiment, the plurality of sensors includes a tire deflection sensor, wherein the controller determines the cone index by identifying an axle vertical weight with the tire deflection sensor and the tire data. In one aspect of this example, the plurality of sensors includes at least one wheel torque sensor, wherein the controller determines the cone index by identifying a pull force related to the wheel torque sensor.

In another example, the plurality of sensors includes a tire pressure sensor that identifies a tire pressure, wherein the controller determines an axle load based on the tire data and the tire pressure.

In yet another example, the tire data includes a tire section height, a tire width, and a tire diameter. In one aspect of this example, the tire data includes a tire deflection ratio.

In another example, the controller repeatedly determines cone index as the work machine moves along the underlying surface. In one aspect of this example, one of the plurality of sensors is a location sensor and the cone index is stored in a memory unit of the controller along with a location that corresponds with the cone index.

Another embodiment is a method for determining a cone index of an underlying surface by providing a work machine having a plurality of sensors communicating with a controller and a first wheel assembly having a first axle and a first tire, storing, in the controller, tire data for the first tire, identifying, with the controller, sensor data at a first time, and determining, with the controller, a cone index of the underlying surface at the first time based on the sensor data and the tire data.

In one example of this embodiment, the work machine has an implement coupler and one of the plurality of sensors is an implement coupler sensor, wherein the controller determines a load on the work machine through the implement coupler with the implement coupler sensor as part of the identifying sensor data step.

In another example, one of the plurality of sensors is a wheel torque sensor, wherein the wheel torque sensor is coupled to the first wheel assembly and sends a wheel torque signal to the controller. Another aspect of this example includes determining a load on the work machine, with the controller, based on the wheel torque signal as part of the identifying sensor data step.

Yet another example includes determining a tire slip of the work machine, with the controller, as part of the identifying sensor data step.

Another example includes providing a tire deflection sensor and an implement sensor wherein the storing tire data step includes storing, in the controller, a tire section height, a tire width, a tire load deflection data, and a tire diameter for the first tire and wherein the identifying sensor data step includes determining, with the controller, a pull load on the work machine with the implement sensor, determining, with the controller, an axle weight with the tire data and the deflection sensor, and determining a slip condition of the work machine with the controller.

Yet another example includes providing a deflection sensor and a wheel torque sensor on the first wheel assembly, wherein the storing tire data step includes storing, in the controller, a tire section height, a tire width, a tire load deflection data set, and a tire diameter for the first tire and wherein the identifying sensor data step includes determining, with the controller, a pull load on the work machine with the wheel torque sensor, determining, with the controller, an axle weight with the tire data and the deflection sensor, and determining a slip condition of the work machine with the controller.

Another example includes providing a location system in communication with the controller to identify a geographic location of the work machine at the first time, wherein the geographic location and the cone index are stored in the controller.

Yet another embodiment is a method for mapping cone index values for an underlying surface including providing a work machine having at least one wheel assembly with a tire, a controller having a processor and a memory unit, a deflection sensor configured to identify a deflection of the tire, a load sensor configured to identify a pulling load of the work machine, a speed sensor configured to identify a true ground speed of the work machine, and a location system, storing tire data in the memory unit of the controller, communicating a pull load signal to the controller with the load sensor to determine the pulling load of the work machine at a first time, determining an axle weight of the work machine, with the controller, based on a deflection signal from the deflection sensor and the tire data at the first time, determining a slip ratio of the work machine, with the controller, based on the speed of the work machine at the first time, calculating a first cone index value at the first time, with the controller, using the tire data, pull load, axle weight, and slip ratio, determining a first geographic position identified by the location system of the work machine at the first time, and storing the first geographic location and the first cone index value in the memory unit of the controller.

One example of this embodiment includes calculating a second cone index value at a second time, determining a second geographic location at the second time, and storing the second geographic location and the second cone index value in the memory unit of the controller.

Another example includes providing a central tire inflation system to selectively alter a tire pressure of the at least one wheel assembly, wherein the controller selects and implements a first tire pressure that corresponds with the first cone index.

In yet another example, the controller stores a plurality of cone index values and a plurality of geographic locations in the memory unit as a cone index map while the work machine moves along the underlying surface.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein.

Corresponding reference numerals are used to indicate corresponding parts throughout the several views.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Figure 1:
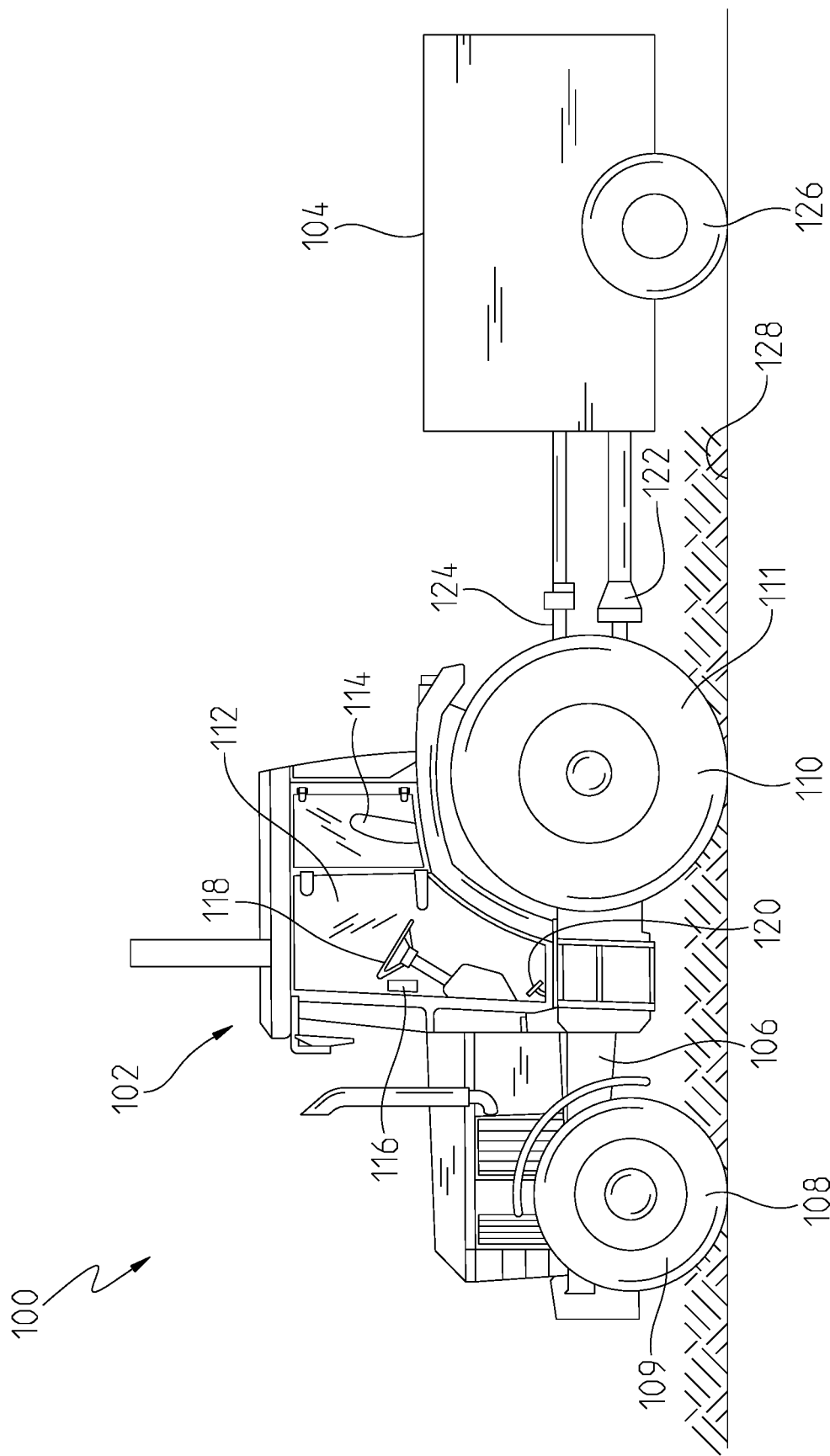
FIG. 1 is a side view of a tractor coupled to a trailer.

Referring to FIG. 1, a combined tractor trailer system 100 is shown. In this system, a tractor 102 is shown coupled to and pulling a trailer 104. The tractor 102 may have a chassis 106 that spans between front ground engaging mechanisms 108 and rear ground engaging mechanisms 110. In the embodiment of FIG. 1, each ground-engaging mechanism is in the form of a wheel having front tires 109 and rear tires 111 coupled thereto and defined along a respective axle, i.e., a front axle and a rear axle. In other embodiments, however, the ground-engaging mechanism may be a track that propels the tractor 102 along an underlying surface 128. Likewise, the trailer 104 may also include at least one ground-engaging mechanism such as a wheel 126.

A cab 112 may be coupled to the chassis 106 and define a location for an operator to be positioned in an operator's seat 114. From the cab, the operator may control the tractor 102 and trailer 104 via a plurality of controls. As shown, the cab 112 may include a display 116 or dashboard that visually shows control characteristics of the tractor 102 or trailer 104 such as speed, power, temperature, pressure, direction, tire pressure, ballast position, and any other type of control characteristic. The display 116 may be a touchscreen display that includes one or more operator controls for selectively controlling the operation of the tractor 102 or trailer 104. Other controls may include a steering wheel or yoke 118, a pedal 120 (e.g., a brake pedal, clutch pedal, or throttle pedal), any other type of control such as a joystick, switch, lever, knob, etc. for controlling the tractor trailer system 100.

While a tractor 102 is shown and described herein, any type of work machine may utilize the teachings of this disclosure and therefore it is not intended to be limited to applying only to tractors. In other embodiments, a truck configured to tow a trailer may utilize the teachings of this disclosure. Further still, in other embodiments work machines utilizing tracks may implement the teachings of this disclosure. Accordingly, the tractor 102 can be any type of work machine used to pull a trailer or perform an entirely different work task.

The tractor 102 may be coupled to the trailer 104 through an implement coupler such as a hitch member or drawbar 122. The hitch member or drawbar 122 may be sufficiently strong to transfer motion of the tractor 102 to the trailer 104. In one embodiment, when the tractor 102 travels in a forward direction, the hitch member or drawbar 122 pulls the trailer 104 along therewith in approximately the same direction. While the implement coupler is described herein as being a hitch member or drawbar 122, other embodiments consider an implement coupler that utilizes a three-point hitch assembly as is known in the art. Accordingly, this disclosure considers many different types of implement couplers.

One or more communication lines 124 may also be provided. The communication lines 124 may provide for electrical communication between the tractor 102 and the trailer 104. More specifically, in one non-exclusive example, the trailer 104 may have an Intelligent Power Management System where the wheels 126 are coupled to an electric motor. In another embodiment, the Intelligent Power Management System may utilize the Power Take-Off to selectively mechanically power the wheels 126. In this embodiment, the communication lines 124 may selectively provide power to the electric motor, hydraulic fluid to a hydraulic motor, or a mechanical linkage to the wheels to thereby power the wheels 126 of the trailer 104.

The trailer 104 or implement shown and described herein is not limited to any particular type of trailer or implement. More specifically, the trailer 104 could also be a tillage implement, a planter, a sprayer or any other implement that is pulled by a work machine or tractor. Accordingly, this disclosure is not limited to the precise trailer shown.

Figure 2:
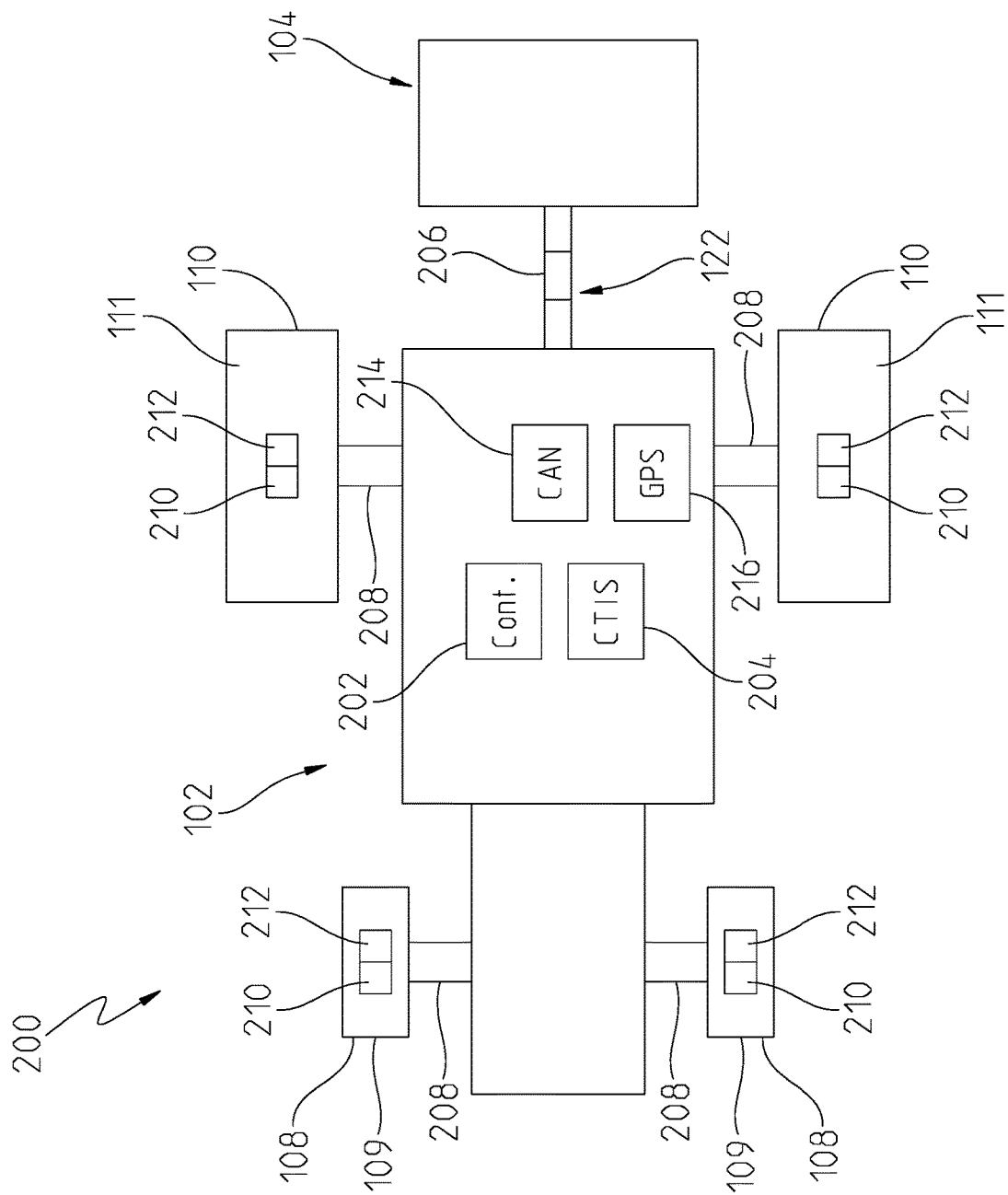
FIG. 2 is a schematic top view of one embodiment of a tractor and trailer system.

Referring now to FIG. 2, a schematic representation 200 of the tractor 102 and trailer 104 is illustrated. In the schematic representation 200, a controller 202 is shown as part of the tractor 102. The controller 202 may have one or more memory unit and processor and be able to control and monitor many components of the tractor 102 and trailer 104. In one example, the controller 202 may communicate with a central tire inflation system 204 (hereinafter "CTIS") to determine and control a tire pressure in any of the tires 109, 111 of the corresponding ground engaging mechanism 108, 110.

The controller 202 may also communicate with a drawbar sensor or other implement coupler sensor 206 positioned to identify the pulling force applied on the trailer 104 with the tractor 102 through the hitch member or drawbar 122 or other implement coupler such as a three-point hitch. The implement coupler sensor 206 may be any type of sensor known in the art capable of determining a load. In one non-exclusive example the implement coupler sensor 206 may be a load cell such as a strain gauge or the like. Alternatively, or in addition to the implement coupler sensor 206, each of the ground engaging mechanisms 108, 110 may have a wheel torque sensor 208 or the like coupled to the corresponding axle, wheel, or other component of the drive system. The wheel torque sensor 208 may identify the torque being distributed through the ground engaging mechanisms 108, 110 to the underlying surface 128. Either one, or both, of the implement coupler sensor 206 or the wheel torque sensors 208 can be analyzed by the controller 202 to determine a pulling force of the tractor 102.

The controller 202 may also be in communication with a tire pressure sensor 210 in chambers for each of the tires 109, 111 of the front and rear ground engaging mechanisms 108, 110. The tire pressure sensor 210 may communicate the tire pressure of the corresponding ground engaging mechanism 108, 110 to the controller 202, the CTIS 204, or both. A tire deflection sensor 212 may be positioned to identify the deflection of the tire 109, 111 to the controller 202. The deflection sensor 212 may be any type of optical based sensor known in the art. Alternatively, the deflection sensor 212 may be acceleration based. Accordingly, this disclosure considers any type of sensor capable of identifying the deflection of a tire.

Regardless of the type of sensor used for the deflection sensor 212, the deflection sensor 212 may be positioned within the cavity of the respective tire 109, 111 or at any other location appropriate for monitoring the distance from the sensor to the inner tire wall. The controller 202 and CTIS 204 may receive deflection information from the deflection sensor 212 to determine a deflection of the corresponding tire 109, 111. The deflection of the tire 109, 111, along with a known tire pressure, may be utilized by the controller 202 to determine an axle vertical weight applied at the tire 109, 111.

While an embodiment utilizing tires is described throughout, this disclosure also considers utilizing work machines that have track assemblies instead of tires. In this configuration, a position sensor may be coupled to the frame and positioned to identify the distance of an unsprung portion of the track assembly and the frame. More specifically, the position sensor may be positioned to identify the position of the suspension system of the track assembly relative to the frame of the tractor. The track position data of the track assembly may be utilized by the controller 202 to determine the axle vertical weight instead of the deflection sensor and tire pressure as described above for a work machine with tires.

The schematic representation 200 may also include a Controller Area Network (hereinafter "CAN") 214. The controller 202 and CTIS 204 may be a part of the CAN 214 or be separate therefrom. The CAN 214 may have one or more electronic control boxes or controllers that communicate with one another to control certain machine components. In one non-limiting example, the CAN 214 may utilize vehicle speed signals from speed sensors along with true vehicle ground speed determined through a Global Positioning System (hereinafter "GPS"), radar, or the like to determine a slip condition between the tires 109, 111 and the underlying surface 128.

The tractor 102 may also have a GPS 216. The GPS 216 may communicate with the controller 202 to identify the geographic location of the tractor 102. Further, the GPS 216 may communicate with the CAN 214 as well to identify an actual vehicle speed based on the different geographic locations identified over time. The GPS 216 may be part of the tractor 102 or an entirely separate assembly. Further, the GPS 216 may be coupled to the trailer 104 rather than the tractor 102. Accordingly, the particular location of the GPS 216 is not limiting.

Figure 3:
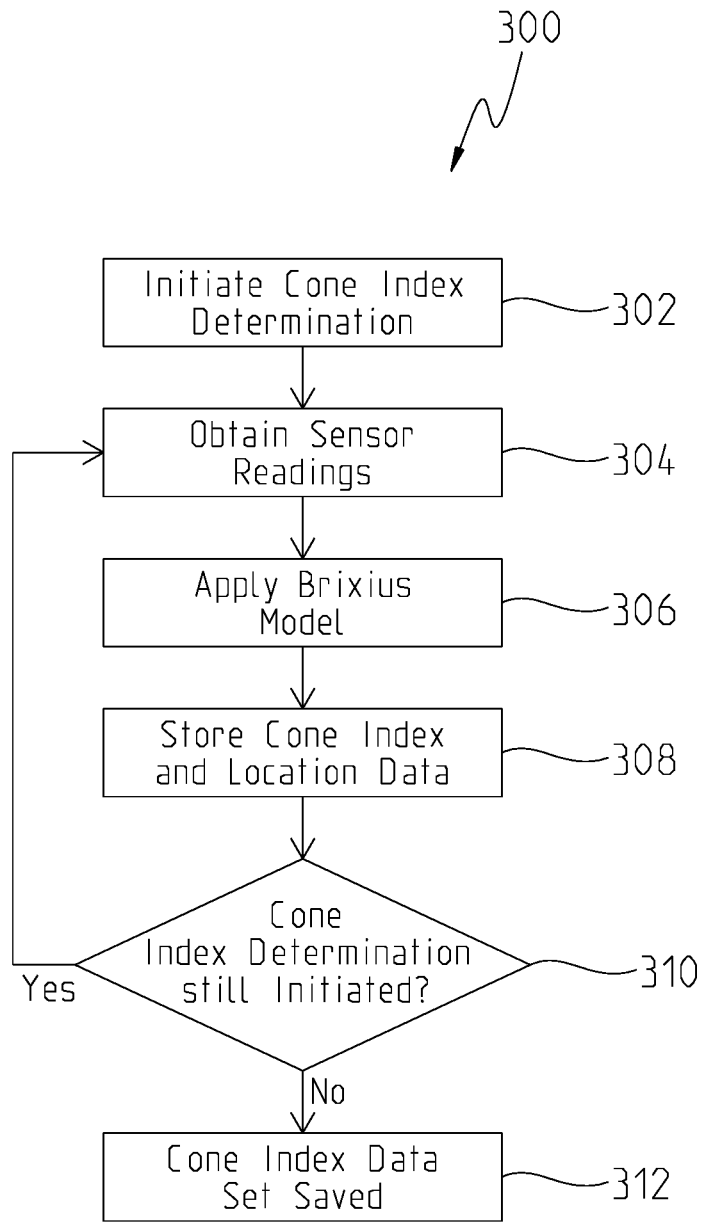
FIG. 3 is a logic flow chart to determine a cone index value with the tractor and trailer system of FIG. 2.

Referring now to FIG. 3, a logic flow chart for determining a cone index 300 is illustrated. The logic flow chart 300 may primarily utilize the system components shown and described in FIGS. 1 and 2. Further, the logic flow chart 300 may apply the Brixius Traction Empirical Model (hereinafter "the Brixius Model") to predict the cone index of the underlying surface 128 of the tractor 102. The Brixius Model as applied to vehicles with tires is as follows:

$$\frac{P}{W} = 0.88\left(1 - e^{-0.08\frac{CIbd}{W}\left(\frac{1+5\frac{\delta}{h}}{1+3\frac{b}{d}}\right)}\right)(1 - e^{9.5s}) - \left(\frac{0.9}{\frac{CIbd}{W}\left(\frac{1+5\frac{\delta}{h}}{1+3\frac{\delta}{d}}\right)} + \frac{0.5s}{\sqrt{\frac{CIbd}{W}\left(\frac{1+5\frac{\delta}{h}}{1+3\frac{b}{d}}\right)}}\right)$$

Brixius Model for Vehicles with Tires

In the above Brixius Model, the "P" represents a pull force acting on the tractor 102 or other work machine. The pull force may be generated, in part, by resistance of the trailer 104 as the tractor 102 pulls the trailer 104 along the underlying surface 128. The pull force may be determined by the controller 202 through communication with the implement coupler sensor 206 which may be a load cell sensor or the like. More specifically, the implement coupler sensor 206 may be positioned along the hitch member or drawbar 122 or other implement coupler to identify the force being transferred there through. The force identified by the implement coupler sensor 206 may be utilized by the controller 202 to identify the pull force of the tractor 102.

In an alternative embodiment, the wheel torque sensors 208 may be utilized instead of the implement coupler sensor 206 to identify the pull force of the tractor 102. In this embodiment, wheel torque sensors 208 may be positioned at each of the ground engaging mechanisms 108, 110 to determine the torque being applied to the ground engaging mechanisms as the tractor 102 travels along the underlying surface 128. The controller 202 may monitor each of the wheel torque sensors 208 to determine the total pull force applied by the tractor 102.

While the implement coupler sensor 206 and the wheel torque sensors 208 are described herein for determining the pull force "P" for the Brixius Model, other sensors and methods may be used as well. In another non-exclusive example, the controller 202 may monitor fuel consumption to determine the pull force exerted by the tractor 102 over time. Further, still, in another embodiment a driveshaft torque sensor may be used to measure the torque applied to the driveshaft. In the embodiment with the driveshaft torque sensor, the measured driveshaft torque can be used by the controller 202 to calculate the wheel axel torque by incorporating a drivetrain gear mesh ratio and efficiency loss expectations. Accordingly, this disclosure considers many different methods for determining pull force.

The "W" of the above Brixius Model represents an axle vertical weight of the tractor 102. The axle vertical weight may be a sum of the axle vertical weights determined at each of the ground engaging mechanisms 108, 110 or the axle vertical weight at each ground engaging mechanism 108, 110. More specifically, the controller 202 may have stored therein dimension data for the specific tire coupled to the corresponding ground engaging mechanism 108, 110. The controller 202 may then utilize the tire pressure sensor 210 and the deflection sensor 212 to determine the tire pressure and deflection of the corresponding tire. The controller 202 may utilize the tire pressure, tire deflection, and tire dimension data to determine the axle vertical weight at each ground engaging mechanism 108, 110. The controller 202 may combine the individual axle vertical weight values from each of the ground engaging mechanisms 108, 110 to determine the total axle vertical weight "W" to be applied in the Brixius Model.

While the tire pressure sensor 210 and the tire deflection sensor 212 are described herein for determining the axle vertical weight "W" for the Brixius Model, other sensor and methods may be used as well. In one non-exclusive example, such as a work machine having a track assembly, a load cell may be utilized to determine the vertical weight "W" by identifying the load of the frame of the tractor on the track assembly. Alternatively, a position sensor may be positioned between the frame and the corresponding axle or other unsprung suspension component to measure the displacement of the suspension component. The displacement of the suspension component may be utilized as a reference for calculating the weight being applied thereto.

The variables "b", "d", and "h" are constants that relate to the tire dimensions. More specifically, "b" may represent the tire width, "d" may represent the tire diameter, and "h" may represent the tire section height. These values may be tire specific and preloaded into the controller 202 to correlate with the corresponding tire used on the ground engaging mechanism 108, 110. Similarly, the variable "δ" is another value preset in the controller 202 based on the particular tire used to determine the deflection ratio "δ/h" of the tire 109, 111.

The "s" variable represents tire slip. As mentioned above, tire slip may be the relative motion between the tire 109, 111 and the underlying surface 128. The tire slip may be determined by the controller 202 or the CAN 214 as a function of theoretical vehicle speed compared to the actual vehicle speed or true ground speed. The theoretical vehicle speed may be determined by the controller 202 or CAN 214 based on engine speed, transmission configuration, axle speed, or any other component of the tractor 102 that correlates with the output to ground engaging mechanisms 108, 110. The actual vehicle speed may be determined utilizing the GPS 216 or the like to determine the actual speed of the tractor 102 relative to the underlying surface. The controller 202 may compare the actual vehicle speed with the theoretical vehicle speed to determine slip.

The numeric values 0.88, 0.08, 9.5, 0.9, and 0.5 may be tire curve fitted parameters pre-loaded into the controller 202. The tire curve fitted parameters are utilized with the remaining variables to determine the cone index with the Brixius Model. As described above, the tractor 102 may have measured or known values for all of the elements of the Brixius Model except for "CI" or the Cone Index. Accordingly, the controller 202 can apply the Brixius Model or other similar algorithm to determine the cone index of the underlying surface as the tractor 102 travels thereon.

In the tracked tractor embodiment, a Brixius Model for Tracked Vehicles may be utilized instead of the Brixius Model for Vehicles with Tires shown above. The Brixius Model for Tracked Vehicles is similar to the Brixius Model for Vehicles with Tires except the variables are configured for tracked vehicles instead of vehicles with tires. More specifically, the pull force "P" may be determined in the same way as described above for the Brixius Model for Vehicles with Tires.

$$\frac{P}{W} = 1.10 \left(1 - e^{-0.025\left(\frac{CI \cdot TW \cdot TL}{W(1-e^{-CI})}\right)\left(\frac{5}{1+6\frac{TW}{TL}}\right)}\right)(1 - e^{17s}) - \left(\frac{1.75}{\left[\left(\frac{CI \cdot TW \cdot TL}{W(1-e^{-CI})}\right)\left(\frac{5}{1+6\frac{TW}{TL}}\right) \cdot 0.7 \cdot \left(1 - \text{abs}\left(\frac{0.7(DWR-1)}{DWR+1}\right)\right)\right]} + \frac{0.5s}{\sqrt{\left(\frac{CI \cdot TW \cdot TL}{W(1-e^{-CI})}\right)\left(\frac{5}{1+6\frac{TW}{TL}}\right)}}\right)$$

Brixius Model for Tracked Vehicles

The axle vertical weight "W" of the Brixius Model for Tracked Vehicles cannot utilize the tire pressure sensor 210 and the tire deflection sensor described above for the Brixius Model for Vehicles with Tires because most tracked vehicle do not have tires. Accordingly, one of the other sensors or methods described above will be used to determine axle vertical weight W for tracked vehicles. In on non-exclusive example a load cell such as a strain gauge or the like may be utilized to determine the vertical weight "W" by identifying the load of the frame of the tractor on the track assembly. The strain gauge may be coupled to an axle or other similar portion of the tractor 102 to identify the load on the axle. Further, the load reading may be utilized to calculate the axle vertical weight W of the tracked vehicle.

Similarly, a position sensor may be positioned between the frame and the corresponding axle or other unsprung suspension component to measure the movement of the axle relative to the frame. The controller 202 may then calculate the axle vertical weight W based on the movement of the axle relative to the frame. A load cell or position sensor may be located at each axle or other coupling point between the tracks and the frame. Accordingly, a sum of the axle vertical weight at each axle may be calculated by the controller 202 to determine the total axle vertical weight W.

The Brixius Model for Tracked Vehicles may also utilize the track width "TW" of the tracks of the vehicle. The track width may be the average width of a cross-section of the tracks. Further, the track length "TL" may also be used by the Brixius Model for Tracked Vehicles. The track length TL may be the length of track that contacts the underlying surface as the tractor 102 sits thereon. In other words, the track length TL is the length of the track that touches the ground at any given time. Both the track width TW and the track length TL may be measured values that can be stored in the controller 202 for calculating the cone index utilizing the Brixius Model for Tracked Vehicles.

The dynamic weight ratio "DWR" is also used by the Brixius Model for Tracked Vehicles. The dynamic weight ratio DWR may be the ratio of weight distribution of the tractor between the front portion and the rear portion of the tracks. In other words, if the tracked vehicle has a left and right track that is coupled to the frame at a front location and at a rear location, the dynamic weight ratio is the ratio of load distribution between the front and rear location of the corresponding left and right track during a neutral state.

In the Brixius Model for Tracked Vehicles, the cone index may be calculated by utilizing the sensors described above to determine the pull force P and the vertical axle weight W. Further, the track width TW, track length TL, and dynamic weight ratio DWR may be measured or otherwise known values. Accordingly, the tractor 102 can utilize the Brixius Model for tracked vehicles along with the data from the sensors and the known values to actively determine cone index as the tractor 102 travels along an underlying surface or field.

While the Brixius Model is described herein, this disclosure also considers other methods for determining cone index. More specifically, in one embodiment the cone index may be determined as part of a lookup table instead of requiring any calculations based on the Brixius model. For example, axle vertical weight, pull load, and slip could all be determined by the controller 202 and applied to a lookup table. The lookup table could correlate the determined vertical weight, pull load, and slip values with a cone index value. Accordingly, one embodiment of the present inventions considers storing in the controller 202 a lookup table that correlates the measured and calculated sensor values with a specific cone index.

Referring back to FIG. 3, the logic flow chart 300 may provide a logic system for the controller 202 to determine the cone index of the underlying surface 128 by applying the Brixius Model to other known and measured values of the tractor 102. More specifically, the logic flow chart 300 may start in box 302, where cone index determination is implemented. The cone index determination may be initiated automatically when the tractor 102 moves or otherwise begins a work process or it may be initiated by an operator either in the cab 112 or remotely. In one non-limiting example, the operator may initiate the cone index determination through the touch screen display 116. Alternatively, a separate user input may be positioned in the cab 112 that the user may engage to initiate the cone index determination of box 302. A person skilled in the art understands the many ways the cone index determination may be initiated and this disclosure is not limited to any particular one.

After the cone index determination is initiated in box 302, the controller 202 may obtain sensor readings in box 304 required to determine the cone index. More specifically, the controller 202 may obtain readings from the deflection sensor 212, the tire pressure sensor 210, and the wheel torque sensor 208 or the implement coupler sensor 206. The controller 202 may store the sensor readings in a memory unit of the controller 202 to refer to the sensor readings when applying them to the Brixius Model. Alternatively, the controller 202 may actively apply the sensor readings obtained in box 304 to the Brixius Model in box 306 to determine the cone index in substantially real time.

In box 306, the controller 202 utilizes the data stored in the memory unit of the controller 202 and the data obtained from the sensors in box 304 to determine the current cone index by applying the Brixius Model to the stored and obtained data. As described above, the stored data includes the tire section height "h", tire width "b", tire diameter "d", tire deflection ratio "δ/h", and the tire curve fitted parameters. Further, the obtained data may include the axle vertical weight "W" obtained based on the deflection and tire pressure sensors, the pull force "P" obtained via the wheel torque sensors 208 or the implement coupler sensor 206, and the slip condition identified by the CAN 214. The controller 202 may apply the Brixius Model as described above to determine the cone index at a given time.

Once the cone index is identified in box 306, the controller 202 may store the cone index value in box 308. More specifically, the controller 202 may store the cone index value identified in box 306 in the memory unit of the controller 202. The controller 202 may also store location data during box 308. The location data may be communicated to the controller 202 from the GPS 216 and comprise geographic coordinates or the like that identify the location of the tractor 102 that corresponds with the particular cone index value being stored.

Next, in box 310, the controller 202 may determine whether the cone index determination is still initiated. Box 310 may be based on substantially the same components described above for box 302. More specifically, the cone index determination of box 310 may identify that the cone index determination is still initiated automatically when the tractor 102 continues to move or otherwise execute the work process. Alternatively, the controller 202 may continue to monitor a user input on the touch screen display 116 and continue to determine cone index unless a user input representing a stop command is selected. Further, the controller 202 may continue to determine cone index as long as the separate user input is engaged. In yet another embodiment, controller 202 may continue to determine cone index as long as an ignition is switched to an "on" position.

If cone index determination remains initiated in box 310, the controller 202 may repeat boxes 304-310 until the cone index determination is no longer initiated. The rate at which the controller 202 repeats boxes 304-310 may be any appropriate rate for the application. More specifically, because tractors typically travel fairly slow and the cone index does not typically change quickly, the controller 202 may cycle through boxes 304-310 at a speed of 1 hertz or slower. Alternatively, if the application calls for greater resolution in cone index mapping, boxes 304-310 may be cycled through at speeds faster than 1 hertz. A person skilled in the art understands that the particular cycle rate may be different and still achieve the desired results of the present disclosure.

In one aspect of the present disclosure, the controller 202 may execute a Kalman Filter when determining the cone index value. The Kalman Filter may utilize, in part, the below Kalman Filter Equations. More specifically, the predicted cone index value at a future time may be the product of the assumed cone index and the potential error. Further, the error may be determined by dividing the assumed cone index by the measured cone index for a given location and time. For further discussion on the mathematical application of the Kalman Filter, see "A New Approach to Linear Filtering and Predictions Problems" by R. E. Kalman and published in the Journal of Basic Engineering in March 1960. While a Kalman Filter is specifically discussed herein, this disclosure is not limited to using a Kalman Filter to address potential noise introduced while applying the Brixius Model.

$$CI_{predicted,t+1} = CI_{assumed,t+1} * k_{error,t}; \text{ where } k_{error,t} = \frac{CI_{assumed,t}}{CI_{measured,t}}$$

Kalman Filter Equations

Once controller 202 determines that cone index determination is no longer initiated, the controller 202 may execute box 312. In box 312, each cone index value and the corresponding GPS location may be stored in a data set file. The data set file may represent a field or other area travelled along while the cone index determination is initiated. Accordingly, the data set may contain an approximate cone index value for each location of the field or other area travelled on as calculated during the recording.

Figure 4:
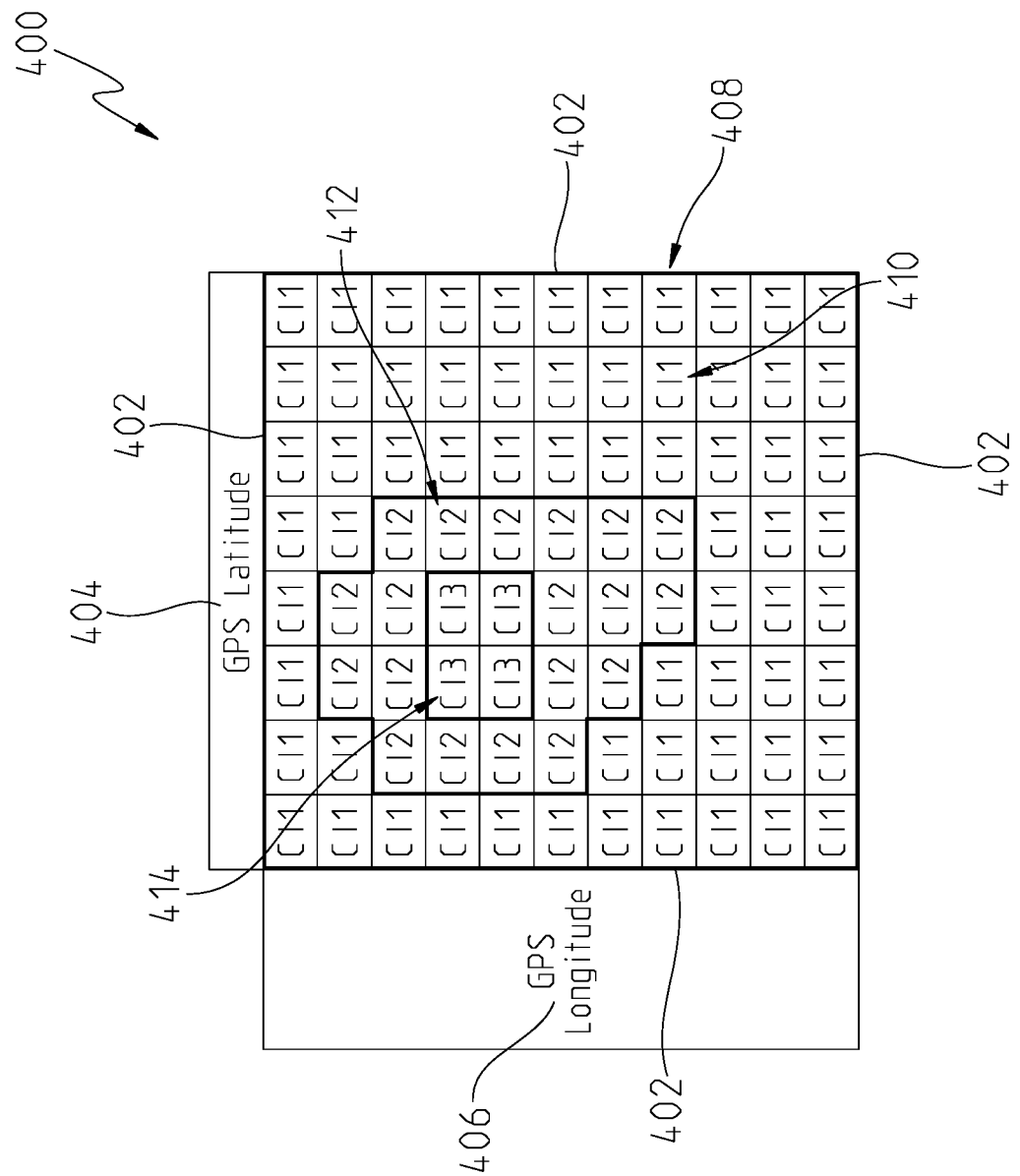
FIG. 4 is an schematic representation of a data set for a field.

Referring now to FIG. 4, one illustrative example of a data set 400 saved in box 312 is shown. The data set 400 may have outer boundaries 402 that represent the outer boundaries of the field on which the tractor 102 travelled while executing the logic flow chart 300. The outer boundaries may be stored as GPS coordinates having a GPS latitude 404 and a GPS longitude 406. Within the outer boundaries 402 may be a plurality of data points 408 that each contain information regarding the cone index value at that particular location. More specifically, each data point 408 may have the specific GPS latitude 404, GPS longitude 406, and cone index value stored therein. Accordingly, the example data set 400 maps the cone index value of the field.

In the non-limiting example of FIG. 4, each data point 408 may have a cone index of "CI1", "CI2", or "CI3." In one example, the cone index value for each data point 408 may have been calculated using the Brixius Model as described above. Accordingly, the exemplary representations of CI1-CI3 are meant only to show that the cone index value may be different throughout the field. Further, FIG. 4 utilizes the references CI1-CI3 for exemplary purposes only. In practice, CI1-CI3 represents the actual measured cone index value stored in the controller 202 for that particular location.

In the non-limiting example of FIG. 4, the illustrative field may have three separate cone index regions. A first region 410 is represented by a cone index value of CI1. In this example, CI1 may be the cone index value of dry soil in any particular region. Each CI1 data point 408 may have been previously calculated by the controller 202 utilizing the logic flow chart 300 shown and described above and saved along with the specific GPS latitude 404 and GPS longitude 406 value for that data point 408.

A second region 412 is represented by a cone index value of CI2. In this example, CI2 may be the cone index value of damp soil in any particular region. Each CI2 data point 408 may have been previously calculated by the controller 202 utilizing the logic flow chart 300 shown and described above and saved along with the specific GPS latitude 404 and GPS longitude 406 value for that data point 408.

Lastly, a third region 414 is represented by a cone index value of CI3. In this example, CI3 may be the cone index value of muddy soil in any particular region. Each CI3 data point 408 may have been previously calculated by the controller 202 utilizing the logic flow chart 300 shown and described above and saved along with the specific GPS latitude 404 and GPS longitude 406 value for that data point 408.

While a first, second, and third region 410, 412, 414, are shown and described herein as having one of three cone index values CI1, CI2, CI3, this disclosure is not limited to any particular number of regions or cone index values. Rather, these regions and exemplary values have been utilized only for illustrative purposes. Accordingly, each data point 408 may have any cone index value and this disclosure is not limited to the examples provided.

In one embodiment, the data set 400 may be used as a reference for the CTIS 204 during future or current use of the field or other area. More specifically, the CTIS 204 may load the data set 400 prior to entering the field or actively determine the data set 400. Next, the tractor 102 may use the CTIS 204 to adjust the tire pressure of the ground engaging mechanisms 108, 110 as the tractor 102 travels along the field. As the tractor approaches an area of the field that has a different cone index, such as entering the first region 410 from the second region 412 or the like, the CTIS 204 may adjust the tire pressure to a tire pressure that will better accommodate the measured cone index.

More specifically, the CTIS 204 or controller 202 may have stored therein a plurality of tire pressure values that correlate with different cone index values or ranges. As one non-exclusive example, a first tire pressure may correlate with CI1, a second tire pressure may correlate with CI2, and a third tire pressure may correlate with CI3. As the tractor 102 travels along the field, the GPS may identify the geographic location of the tractor 102 and the CTIS 204 may adjust the tire pressure to the appropriate pressure in view of the cone index value identified in the data set 400 for that particular geographic location.

Figure 5:
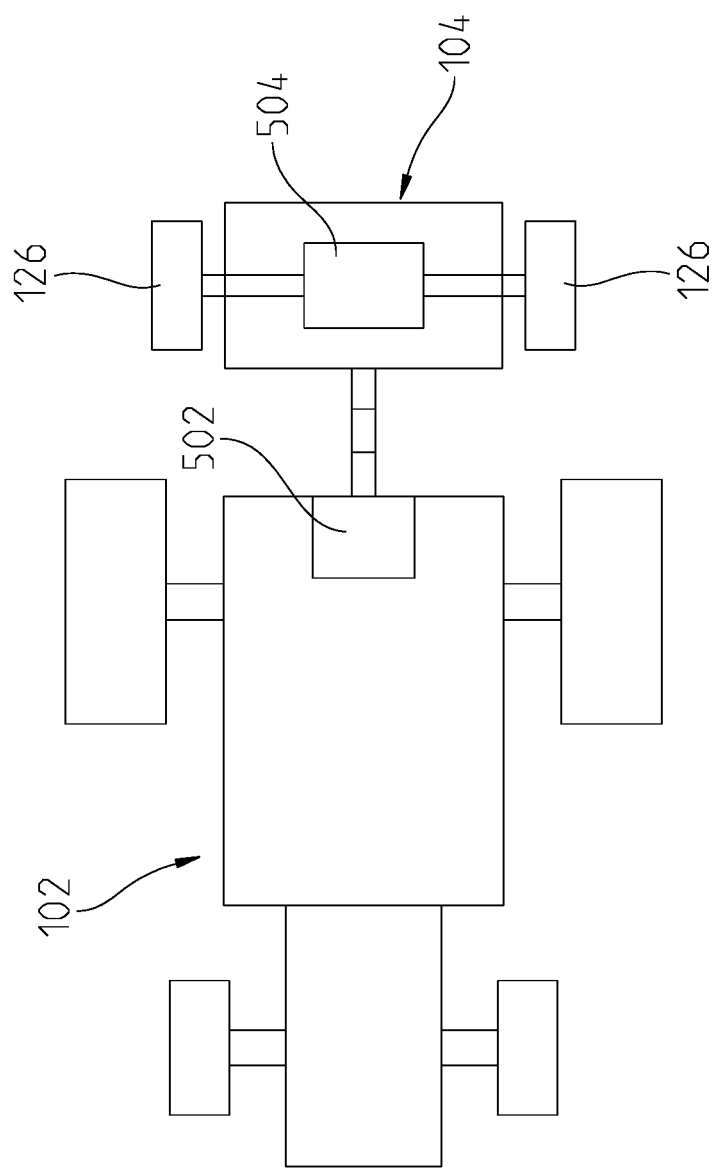
FIG. 5 is a schematic top view of another embodiment of a tractor and trailer system having intelligent power management.

FIG. 5 illustrates another embodiment where the tractor 102 may have Intelligent Power Management (hereinafter "IPM"). The IPM may utilize a generator 502 on the tractor 102 to provide power to an electric motor 504 that is mechanically coupled to the wheels 126 of the trailer 104. The electric motor 504 may selectively drive the wheels 126 of the trailer 104 to provide supplemental traction to the tractor 102. In one aspect of this embodiment, the amount of torque provided to the wheels 126 of the trailer 104 may be variable. In this embodiment, the IPM may vary the amount of torque provided to the wheels 126 of the trailer 104 based on the cone index value identified in the data set 400 for that region.

In one nonexclusive example the IPM may provide 100% available torque to the wheels 126 when the tractor 102 is in the third region 414, 75% available torque to the wheels 126 when the tractor 102 is in the second region 412, and 50% available torque to the wheels 126 when the tractor 102 is in the first region 410. In other words, the IPM utilizes the calculated or previously recorded cone index value for a given geographic area to select the proper supplemental torque setting for the electric motor 504.

While specific percentages of available torque are given herein for the electric motor 504 as it becomes positioned within the exemplary regions 410, 412, 414, this disclosure is not limited to any particular torque percentage. Rather, this disclosure considers that any range of available torque percentages could be applied to any range of cone index values. More specifically, higher available torque percentages may be utilized when the cone index value indicates there is limited traction and less or none of the available torque may be applied to the wheels 126 when the cone index identifies ideal traction conditions. Further, the available torque percentage may be any value in the 0-100 percent range depending on the cone index.

Figure 6:
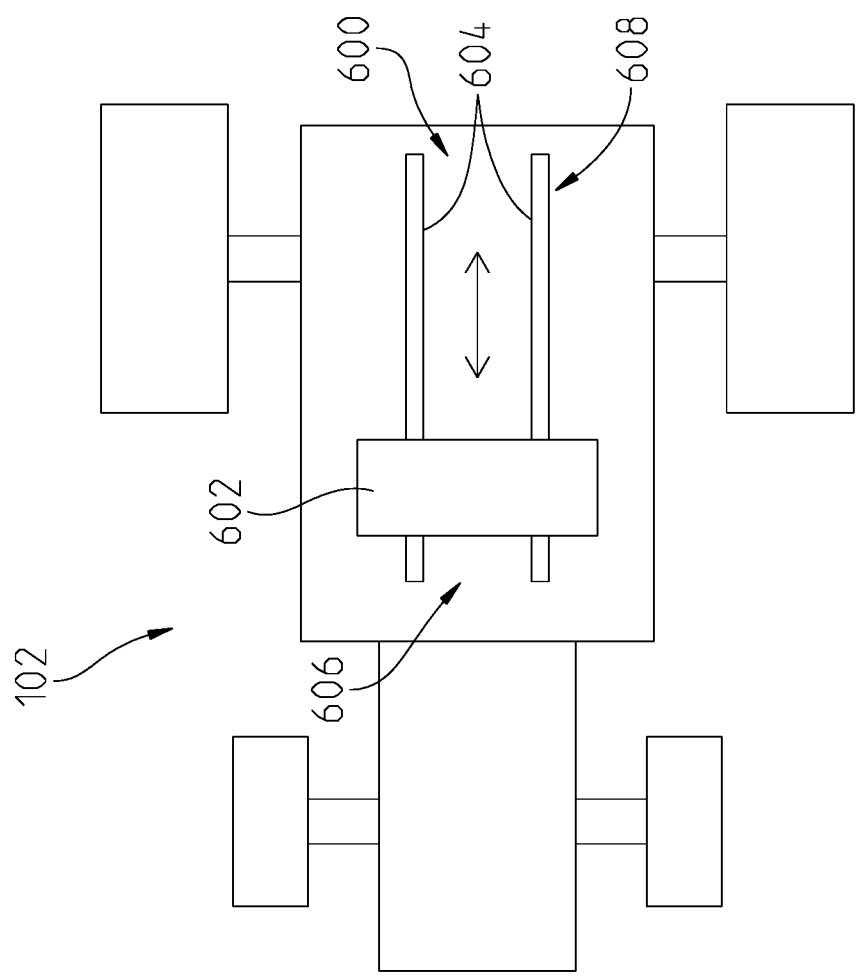
FIG. 6 is a schematic top view of another embodiment of a tractor having a dynamic ballast system.

Now referring to FIG. 6, in a different embodiment the tractor 102 may adjust a ballast system 600 responsive to a change in cone index value as the tractor 102 moves along the field. More specifically, the tractor 102 may have a ballast weight 602 that is selectively positionable along ballast rails 604 between a front portion 606 and a rear portion 608. In this embodiment, the controller 202 may reposition the ballast weight 602 along the rails 604 to be biased towards the front portion 606 or the rear portion 608. In this embodiment, the cone index value may be considered when the controller 202 determines the proper location for the ballast weight 602 along the rails 604. More specifically, in one non-exclusive example, the controller 202 may position the ballast weight 602 towards the rear portion 608 when the tractor 102 is in the first region 410, between the front and rear portion 606, 608 when the tractor is in the second region 412, and towards the front portion 606 when the tractor 102 is in the third region 414.

The particular locations described above for the ballast weight 602 are meant only as examples. Accordingly, other ballast weight 602 locations are also considered herein. More specifically, the controller 202 may monitor the recorded or measured cone index of the particular location of the tractor 102 and adjust the ballast weight 602 to any appropriate corresponding location along the rails 604. Accordingly, this disclosure is not limited to any particular location of the ballast weight 602 responsive to the cone index.

In one aspect of this disclosure, a combination of all of the above embodiments may be implemented on a tractor or other work machine. More specifically, the tire pressure may be adjusted via the CTIS 204, the percentage of available torque applied to the electric motor 504 in the IPM may be adjusted, and the location of the ballast weight 602 may be altered responsive to a change in the calculated or previously recorded cone index. Any combination of the above-described systems may be implemented with one another and this disclosure considers combinations that aren't expressly described as well.

While this disclosure has been described with respect to at least one embodiment, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this pertains and which fall within the limits of the appended claims.

The invention claimed is:

1. A work machine, comprising:
   a chassis;
   a wheel hub rotationally coupled to the chassis;
   a tire coupled to the wheel hub and configured to engage an underlying surface; and
   a controller communicating with a plurality of sensors and having a memory unit;
   wherein, the controller stores tire data for the tire in the memory unit;
   wherein, the controller determines a cone index of the underlying surface of the work machine based on the tire data and the plurality of sensors;
   wherein one of the plurality of sensors is a location sensor and the cone index is stored in a memory unit of the controller along with a location of the cone index as determined by the location sensor; and
   wherein the controller adjusts a tire pressure of the tire as the work machine travels along the underlying surface based on the stored cone index value and the location that corresponds to the stored cone index value.

2. The work machine of claim 1, further wherein the plurality of sensors includes a tire deflection sensor, wherein the controller determines the cone index by identifying an axle vertical weight with the tire deflection sensor and the tire data.

3. The work machine of claim 2, further wherein the plurality of sensors includes at least one wheel torque sensor, wherein the controller determines the cone index by identifying a pull force with the wheel torque sensor.

4. The work machine of claim 1, wherein the plurality of sensors includes a tire pressure sensor that identifies the tire pressure, wherein the controller determines an axle load based on the tire data and the tire pressure.

5. The work machine of claim 1, wherein the tire data includes a tire section height, a tire width, and a tire diameter.

6. The work machine of claim 5, further wherein the tire data includes a tire deflection ratio.

7. The work machine of claim 1, further wherein the controller applies a Kalman filter when the controller determines the cone index.

8. A method for determining a cone index of an underlying surface, comprising:
   providing a work machine having a plurality of sensors communicating with a controller and a first wheel assembly having a first axle and a first tire having a tire pressure;
   storing, in the controller, tire data for the first tire;
   identifying, with the controller, sensor data at a first time;
   determining, with the controller, a cone index of the underlying surface at the first time based on the sensor data and the tire data;
   providing a location system in communication with the controller to identify a geographic location of the work machine at the first time, wherein the geographic location corresponds to the cone index, and the geographic location and cone index are stored in the controller; and
   providing, by the controller, an adjustment to the tire pressure based on the cone index for the underlying surface corresponding to the geographic location at the first time.

9. The method for determining cone index of claim 8, further wherein the work machine has an implement coupler and one of the plurality of sensors is an implement coupler sensor, wherein the controller determines a load on the work machine through the implement coupler with the implement coupler sensor as part of the identifying sensor data step.

10. The method for determining cone index of claim 8, further wherein one of the plurality of sensors is a wheel torque sensor, wherein the wheel torque sensor is coupled to the first wheel assembly and sends a wheel torque signal to the controller.

11. The method for determining a cone index of claim 10, further comprising determining a load on the work machine, with the controller, based on the wheel torque signal as part of the identifying sensor data step.

12. The method for determining a cone index of claim 8, further comprising determining a tire slip of the work machine, with the controller, as part of the identifying sensor data step.

13. The method for determining a cone index of claim 8, further comprising:
providing a tire deflection sensor and an implement sensor;
wherein the storing tire data step, comprises:
  storing, in the controller, a tire section height, a tire width, a tire load deflection data, and a tire diameter for the first tire;
wherein the identifying sensor data step comprises:
  determining, with the controller, a pull load on the work machine with the implement sensor;
  determining, with the controller, an axle weight with the tire data and the deflection sensor; and
  determining a slip condition of the work machine with the controller.

14. The method for determining a cone index of claim 8, further comprising:
providing a deflection sensor and a wheel torque sensor on the first wheel assembly;
wherein the storing tire data step, comprises:
  storing, in the controller, a tire section height, a tire width, a tire load deflection data set, and a tire diameter for the first tire;
wherein the identifying sensor data step comprises:
  determining, with the controller, a pull load on the work machine with the wheel torque sensor;
  determining, with the controller, an axle weight with the tire data and the deflection sensor; and
  determining a slip condition of the work machine with the controller.

15. The method for determining a cone index of claim 8, further comprising providing a location system in communication with the controller to identify a geographic location of the work machine at the first time, wherein the geographic location and the cone index are stored in the controller.

16. A method for determining a cone index of an underlying surface, comprising:
providing a work machine having a plurality of sensors communicating with a controller;
storing, in the controller, vehicle data;
identifying, with the controller, sensor data at a first time, wherein the sensor data includes a tire pressure identified by a tire pressure sensor; and
calculating, with the controller, a cone index of the underlying surface at the first time based on the sensor data and the vehicle data, and an adjustment to the tire pressure based on the calculated cone index for the underlying surface at the first time.

17. The method of claim 16, further wherein the sensor data identified by the controller includes a load cell configured to identify an axle vertical weight and the vehicle data includes a track width and a track length.

18. The method of claim 16, further wherein the sensor data identified by the controller includes a deflection sensor configured to identify the deflection and the vehicle data includes a tire section height.

19. The method of claim 16, further wherein the sensor data includes data from a load cell.

20. The work machine of claim 1, wherein the controller stores a plurality of cone index values and a plurality of particular geographic locations as a cone index map while the work machine moves along the underlying surface, each of the plurality of particular geographic locations identified by one the plurality of cone index values and wherein the controller determines a value to adjust the tire pressure of the tire for each of the particular geographic locations of the vehicle of the cone index map.

* * * * *